United States Patent
Berge (10) Patent No.: US 7,378,443 B2
(45) Date of Patent: *May 27, 2008

(54) FATTY ACID ANALOGUES FOR THE TREATMENT OF CANCER

(75) Inventor: Rolf Berge, Bones (NO)

(73) Assignee: Thia Medica, AS, Bergen (NO)

( * ) Notice: Subject to any disclaimer, the term of this patent is extended or adjusted under 35 U.S.C. 154(b) by 0 days.

This patent is subject to a terminal disclaimer.

(21) Appl. No.: 10/312,901

(22) PCT Filed: Jul. 13, 2001

(86) PCT No.: PCT/NO01/00301

§ 371 (c)(1),
(2), (4) Date: Jan. 2, 2003

(87) PCT Pub. No.: WO02/03983

PCT Pub. Date: Jan. 17, 2002

(65) Prior Publication Data

US 2004/0024063 A1    Feb. 5, 2004

(30) Foreign Application Priority Data

Jul. 13, 2000    (NO)    .................. 20003591

(51) Int. Cl.
*A61K 31/22*    (2006.01)
*A61K 31/23*    (2006.01)
*A61K 31/20*    (2006.01)

(52) U.S. Cl. ............... 514/549; 514/550; 514/552; 514/558; 514/560

(58) Field of Classification Search ........... 514/549, 514/550, 552, 558, 560
See application file for complete search history.

(56) References Cited

U.S. PATENT DOCUMENTS

| | | | | |
|---|---|---|---|---|
| 5,750,515 | A | * | 5/1998 | Shibata et al. ............... 514/63 |
| 6,046,237 | A | * | 4/2000 | Berge et al. ............... 514/546 |
| 6,358,915 | B1 | * | 3/2002 | Patierno et al. ............. 514/2 |
| 7,026,356 | B2 | * | 4/2006 | Berge ..................... 514/546 |

FOREIGN PATENT DOCUMENTS

WO    WO 97/03663    *    2/1997

OTHER PUBLICATIONS

Cecil Texbook of Medicine, Goldman et al. (eds.), 21st Edition, vol. 1, published 2000 by W.B.Saunders Co. (PA), pp. 1060-1074.*

* cited by examiner

*Primary Examiner*—Raymond J. Henley, III
(74) *Attorney, Agent, or Firm*—Reed Smith LLP; Stanley P. Fisher, Esq.; Juan Carlos A. Marquez, Esq.

(57) ABSTRACT

A fatty acid analogue of the general formula: $R_1-[x_i-CH_2]_n-COOR_2$, wherein $R_1$ is: a $C_2-C_{24}$ alkene with one or more double bonds and/or with one or more triple bonds, and/or a $C_2-C_{24}$ alkyne, and/or a $C_1-C_{24}$ alkyl, or a $C_1-C_{24}$ alkyl substituted in one or several positions with one or more compounds selected from the group comprising fluoride, chloride, hydroxy, $C_1-C_4$ alkoxy, $C_1-C_4$ alkylthio, $C_2-C_5$ acyloxy or $C_1-C_4$ alkyl, and wherein R2 represents hydrogen or $C_1-C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and or a salt, prodrug or complex thereof is used in the treatment and/or prevention of primary and secondary metastatic neoplasms.

22 Claims, 5 Drawing Sheets

FATTY ACID ANALOGUES FOR THE TREATMENT OF CANCER

The present invention relates to fatty acid analogues which can be used for the treatment and/or prevention of cancer. More specifically, the invention relates to the use of the fatty acid analogues for the treatment and/or inhibition of primary and secondary neoplasms.

BACKGROUND OF THE INVENTION

Treatment with modified fatty acids of the present invention represents a new way to treat these diseases.

EP 345.038 describes the use of non-β-oxidizable fatty acid analogues for the treatment of hyperlipidaemic conditions and for reducing the concentration of cholesterol and triglycerides in the blood of mammals.

PCT/N095/00195 describes alkyl-S—$CH_2COOR$ and alkyl-Se—$CH_2COOR$ for the inhibition of the oxidative modification of LDL, and for the reduction of the proliferation of cancer cells. However, this proliferative effect is cell spesific, and we have shown that the compounds of the present invention in other cell systems have no effect on cell growth or proliferation.

PCT/NO99/00135, 00136 and 00149 describe the use of the fatty acid analogues for the treatment of obesity, diabetes and stenosis.

It has now been found that the analogues described in the prior art publications mentioned above, i.e. the non-β-oxidizable fatty acids in accordance with the present invention have broader area of applications. We have shown that the compounds of the present invention inhibit the growth and metastatic behaviour of tumours, and increase the overall survival of animals with implanted tumours.

CANCER

The development of new and more effective chemotherapeutic agents for cancer treatment requires consideration of a variety of factors including cytotoxicity, tumour cell proliferation, invasion and metastasis. Conventional anticancer agents have typically been identified on the basis of their cytotoxicity alone.

Tumour progression is thought to occur when variant cells having selective growth properties arise within a tumour cell population, and one of the final stages of tumour progression is the appearance of the metastatic phenotype. During metastasis, the tumour cells invade the blood vessels, survive against circulating host immune defences, and then extravasate, implant, and grow at sites distant from the primary tumour. This ability of tumour cells to invade neighbouring tissues and to colonise other organs is among the leading causes of cancer related deaths.

The term metastasis encompasses a number of phenotypic traits which together result in the clinical problem that most often leads to death from cancer. The cells lose their adherence and restrained position within an organised tissue, move into adjacent sites, develop the capacity both to invade and to egress from blood vessels, and become capable of proliferating in unnatural locations or environments. These changes in growth patterns are accompanied by an accumulation of biochemical alterations which have the capacity to promote the metastatic process.

So far, little is known about the intrinsic mechanism involved in the metastatic cascade. It is likely that in some cases the augmented metastatic potential of certain tumour cells may be due to an increased expression of oncogenes, which normally are responsible for control of various cellular functions, including differentiation, proliferation, cell motility, and communication. Further, it has been shown that substances that modulate signal transduction pathways can inhibit the metastatic behaviour of a tumour, and it is also speculated that compounds with surface related effects, e.g. compounds which modulates the cell membranes, might be involved in the process leading to metastasis.

Cancer is a disease of inappropriate tissue accumulation. This derangement is most evident clinically when tumour tissue bulk compromises the function of vital organs. Contrary to what is generally thought, human malignant disorders are usually not diseases of rapid cell proliferation. In fact, the cells of most common cancers proliferate more slowly than many cells in normal tissues. It is a relatively slow accumulation of tumour tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity.

Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumours are composed mostly of non-cycling cells, it is not surprising that chemotherapy is not always effective in eradicating cancer.

The strategy of cancer treatment is to shift tumour cells from a non-cycling compartment to a cycling compartment. Several methods that promote this shift form the basis for combined-modality treatment. Surgery is most commonly used to reduce tumour size and thus facilitate re-entry of cancer cells into the cell cycle. After the primary tumour is completely removed, microscopic metastases may remain at distant sites. Because of their small size, the micrometastases are composed principally of cycling cells. Small numbers of cells that remain at primary tumour site are also likely to re-enter the cell cycle. Thus, the remaining cancer cells are often susceptible to chemotherapy. Radiation therapy or chemotherapy alone can also be used to reduce tumour bulk and thus recruit cells into the cycling cell compartment.

Combination drug therapy is, therefore, the basis for most chemotherapy employed at present. Combination chemotherapy uses the different mechanisms of action and cytotoxic potentials of multiple drugs.

However, even though the chemotherapeutic agents are more effective in killing or damaging malignant cells than normal cells, the fact that they do harm normal cells indicates their great potential for toxicity. For chemotherapy to be effective, the patient must be in good physiologic condition.

Cancer treatment requires inhibition of a variety of factors including tumour cell proliferation, metastatic dissemination of cancer cells to other parts of the body, invasion, tumour-induced neovascularization, and enhancement of host immunological responses and cytotoxicity. Conventional cancer chemotherapeutic agents have often been selected on the basis of their cytotoxicity to tumour cells. However, some anticancer agents have adverse effects on the patient's immunological system. Unfortunately, for the vast majority of conventional antineoplastic agents the margin between an effective dose and a toxic dose, i.e., the therapeutic index, is extremely low. Thus, it would be greatly advantageous if a cancer therapy or treatment could be developed that would afford noncytotoxic protection against factors that might lead to growth, progression and metastasis of invasive cancers.

The present invention is directed to a method for the prevention and/or treatment of primary and metastatic neoplasms that involves using a fatty acid analogues of the present invention to treat a patient suffering from a cancer.

The two essential features of cancer are invasion and metastasis. At one extreme, microinvasion of the basement membrane characterises the transition from neoplasia to cancer, and at the other extreme, metastases generally lead to death.

Invasion into the underlying connective tissue by primary tumour proceeds in stages and is facilitated by various mediators produced by the tumour cells. Tumour cells that have not invaded the basement membrane and remain confined within the epithelium are termed carcinoma in situ.

Metastases, on the other hand, may form when circulating tumour cells with adherent lymphocytes and platelets are trapped in capillaries and the tumour cell membrane interacts with the capillary endothelium. The capillary endothelial junctions retract, and tumour cell ligands bind to receptors on the endothelial and basement membranes. Tumour cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumour cells then may proliferate and synthesise platelet aggregatory factors such as thromboxanes and procoagulants, thereby leading to the deposition of a fibrin cocoon around the cells. Such a cocoon may protect the micrometastasis from attack by the host's immune system.

Cancers that can be prevented and/or treated by the compositions and methods of the present invention include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chordoma, angiosarcoma, endothelio-sarcoma, lymphangiosarcoma, lymphangioendotheliosarcoma, synovioma, mesothelioma, Ewing's tumour, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below We have shown that the compound of the present invention decreases the average diameter of various spheroids and that the tumour volume of BT4Cn tumours decreases. Further, we have shown that the overall survival of TTA treated rats with implanted tumours is substantially increased.

Thus, the fatty acid analogues of the present invention have been proved to have a marked effect on the growth, invasion and metastasis of tumours.

Tetradecylthioacetic acid (TTA) is most thoroughly studied compound of the present invention, and we have shown several beneficial effects in various in vitro and in vivo test systems.

DETAILED DESCRIPTION OF THE INVENTION

The present invention discloses that modified fatty acid analogues at non-cytotoxic concentrations can be used for the treatment and/or prevention of cancer.

The present invention relates to the use of fatty acid analogues of the general formula (I):

$$R_1\text{-}[x_i\text{-}CH_2]_n\text{—}COOR_2 \qquad (I)$$

wherein $R_1$ is;
- a $C_1$-$C_{24}$ alkene with one or more double bonds and/or with one or more triple bonds, and/or
- a $C_1$-$C_{24}$ alkyne, and/or
- a $C_1$-$C_{24}$ alkyl, or an alkyl substituted in one or several positions with one or more compounds selected from the group comprising fluoride, chloride, hydroxy, $C_1$-$C_4$ alkoxy, $C_1$-$C_4$ alkylthio, $C_2$-$C_5$-acyloxy or $C_1$-$C_4$ alkyl, and wherein $R_2$ represents hydrogen or $C_1$-$C_4$ alkyl, and
wherein n is an integer from 1 to 12, and
wherein i is an odd number and indicates the position relative to $COOR_2$, and
wherein $X_i$ independent of each other are selected from the group comprising O, S, SO, $SO_2$, Se and $CH_2$, and with the proviso that at least one of the $X_i$ is not $CH_2$, or a salt, prodrug and complex thereof, for the preparation of a pharmaceutical composition for the treatment and/or inhibition of primary and secondary metastatic neoplasms.

Presently preferred embodiments of the present invention relates to the compounds tetradecylthioacetic acid (TTA) and tetradecylselenioacetic acid (TSA)

More specifically, the invention relates to the use of the compounds for the inhibition of the growth, invasive and metastatic properties of tumours.

A further aspect of the invention relates to a method for the treatment and/or inhibition of primary and secondary metastatic neoplasms, said method comprising the step of administering to a mammal in need thereof an effective amount of fatty acid analogues of the general formula (I):

$$R_1\text{-}[x_i\text{-}CH_2]_n\text{—}COOR_2 \qquad (I)$$

wherein $R_1$ is;
- a $C_1$-$C_{24}$ alkene with one or more double bonds and/or with one or more triple bonds, and/or
- a $C_1$-$C_{24}$ alkyne, and/or
- a $C_1$-$C_{24}$ alkyl, or an alkyl substituted in one or several positions with one or more compounds selected from the group comprising fluoride, chloride, hydroxy, $C_1$-$C_4$ alkoxy, $C_1$-$C_4$ alkylthio, $C_2$-$C_5$ acyloxy or $C_1$-$C_4$ alkyl, and wherein $R_2$ represents hydrogen or $C_1$-$C_4$ alkyl, and
wherein n is an integer from 1 to 12, and wherein i is an odd number and indicates the position relative to COOR$_2$, and wherein X$_i$ independent of each other are selected from the group comprising O, S, SO, SO$_2$, Se and CH$_2$, and with the proviso that at least one of the X$_i$ is not CH$_2$, or a salt, prodrug and complex thereof.

The treatment involves administering to a mammal in need of such treatment a therapeutically effective concentration which is maintained substantially continuously in the blood of the animal for the duration of the period of its administration.

ADMINISTRATION OF THE COMPOUNDS OF THE PRESENT INVENTION

As a pharmaceutical medicament the compounds of the present invention may be administered directly to the mammal by any suitable technique, including parenterally, intranasally, orally, or by absorption through the skin. They can be administered locally or systemically. The specific route of administration of each agent will depend, e.g., on the medical history of the animal.

Examples of parenteral administration include subcutaneous, intramuscular, intravenous, intraarterial, and intraperitoneal administration.

As a general proposition, the total pharmaceutically effective amount of each of the compounds administered parenterally per dose will preferably be in the range of about 5 mg/kg/day to 1000 mg/kg/day of patient body weight, although, as noted above, this will be subject to a great deal of therapeutic discretion. For TTA it is expected that a dose of 100-500 mg/kg/day is preferable, and for TSA the dosage could probably in the range of from 10 to 100 mg/kg/day.

If given continuously, the compounds of the present invention are each typically administered by 1-4 injections per day or by continuous subcutaneous infusions, for example, using a mini-pump. An intravenous bag solution may also be employed.

For parenteral administration, in one embodiment, the compounds of the present invention are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the compounds of the present invention each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier may suitably contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDT'A sugar alcohols such as mannitol or sorbitol; counterions such as sodium; and/or non-ionic surfactants such as polysorbates, poloxamers, or PEG.

For oral pharmacological compositions such carrier material as, for example, water, gelatine, gums, lactose, starches, magnesium-stearate, talc, oils, polyalkene glycol, petroleum jelly and the like may be used. Such pharmaceutical preparation may be in unit dosage form and may additionally contain other therapeutically valuable substances or conventional pharmaceutical adjuvants such as preservatives, stabilising agents, emulsifiers, buffers and the like. The pharmaceutical preparations may be in conventional liquid forms such as tablets, capsules, dragees, ampoules and the like, in conventional dosage forms, such as dry ampoules, and as suppositories and the like.

In addition, the compounds of the present invention are appropriately administered in combination with other treatments for combating or preventing cancer.

The invention will be more fully understood by reference to the following examples. They should not, however, be construed as limiting the scope of the invention.

EXPERIMENTAL SECTION

Example 1

Preparation and Characterisation of the Compounds

The Synthesis of 3-Substituted Fatty Acid Analogues

The compounds used according to the present invention wherein the substituent $x_{i=3}$ is a sulphur atom or selenium atom may be prepared according to the following general procedure:

X is a Sulphur Atom:

The thio-substituted compound used according to the present invention may be prepared by the general procedure indicated below:

Alkyl—Hal + HS—CH$_2$COOR $\xrightarrow{\text{Base}}$ Alkyl—S—CH$_2$—COOR

The sulphur-compound, namely, tetradecylthioaceticacid (TTA), (CH$_3$—(CH$_2$)$_{13}$—S—CH$_2$—COOH was prepared as shown in EP-345.038.

X is a Selenium Atom:

the seleno-substituted compound used according to the present invention may be prepared by the following general procedure 1. Alkyl-Hal+KSeCN ⇒Alkyl-SeCN ...
2. Alkyl-SeCN+BH$_4^-$ ⇒Alkyl-Se$^-$
3. Alkyl-Se$^-$+O$_2$ ⇒Alkyl-Se-Se-Alkyl This compound was purified by carefully crystallisation from ethanol or methanol.

5. Alkyl-Se$^-$+Hal-CH$_2$_COOH ⇒Alkyl-Se-CH$_2$—COOH

The final compound, e.g. when alkyl is tetradecyl, (CH$_3$—(CH$_2$)$_{13}$—Se—CH$_2$—COOH (tetradecylselinioacetic acid (TSA)) can be purified by crystallisation from diethyl ether and hexane.

Other compounds in accordance with the present invention can be synthesised as indicated in applicant patent applications PCT/NO99/00135 and NO 20001123.

Example 2

Toxicity Study of TTA

A 28 days toxicity study in dogs according to GLP guidelines has been performed by Corning Hazleton (Europe), England. Oral administration of TTA at dose levels up to 500 mg/kg/day was generally well tolerated. Some lipid related parameters were lowered in the animals given high dosages. This is consistent with the pharmacological activity of TTA. There was no evidence of toxicity at dose levels of 50 or 500 mg/day/kg.

Covance Laboratories Limited, England, has performed tests for mutagenic activity. It was concluded that TTA and TSA did not induce mutations in strains of *Salmonella typhimurium* and *Escherichia coli*. Furthermore, TTA was not mutagenic when tested in mouse lymphoma cells and L5178Y.

The concentration of the compounds tested in *S. typhimurium* and *E. coli* were 3-1000 mg/plate (TTA) 2-5000 mg/plate (TSA). In mouse lymphoma cells, L5178Y, the concentration was 2,5-50 mg/ml.

TSA and TSA were found not to be mutagenic in these tests. TSA and TTA have been tested for chromosomal aberrations in cultured Chinese hamster ovary cells and no aberrations were induced by the doses tested (12-140 mg/ml).

The compounds of the present invention are therefore potentially useful as pharmaceutical compounds in this respect.

Example 3

The Effect TTA on the Spheroid Growth

Multicellular tumour spheroids were obtained by seeding 3×10$^6$ cells into 80 cm$^2$ tissue culture flasks base coated with a 10 ml (KB/KJT=20 ml) 0.75%-.agar DMEM solution (KB/KJT=3%). After 7 days incubation, spheroids with diameters between 100 and 300 µm were selected with a Pasteur pipette under a stereomicroscope. The spheroid size was determined by using an inverted microscope with a calibrated reticule in the eyepiece.

To compare the effect of the different fatty acid analogues on tumour spheroid growth, both D-54Mg and GaMg spheroids were transferred individually into 16 mm 24-well dishes base coated with 0.5 ml 0.75% DMEM-agar. D-54Mg and GaMg are human cell lines. The D-54Mg cell line was derived from a mixed anaplastic glioma and was kindly supplied by Dr. Darell D. Bigner, Duke University, Durham, N.C. The GaMg cell line was established in our laboratory and has been described in detail elsewhere (Bjerkvik et al.: Anticancer research 1998: vol 8, p 797-803). The spheroids were divided into 5 groups with 4 spheroids in each group. Four groups were treated with the different fatty acid analogues at a final fatty acid concentration of either 100 or 250 µM. The fifth group (control) did not receive any treatment. The volume of the overlay suspension was 1.0 ml. The size of the spheroids were determined every second day be measuring two orthogonal diameters using an inverted phase contrast microscope with a calibrated reticle in the eyepiece. This was done during a 14-day period.

Figure 1:
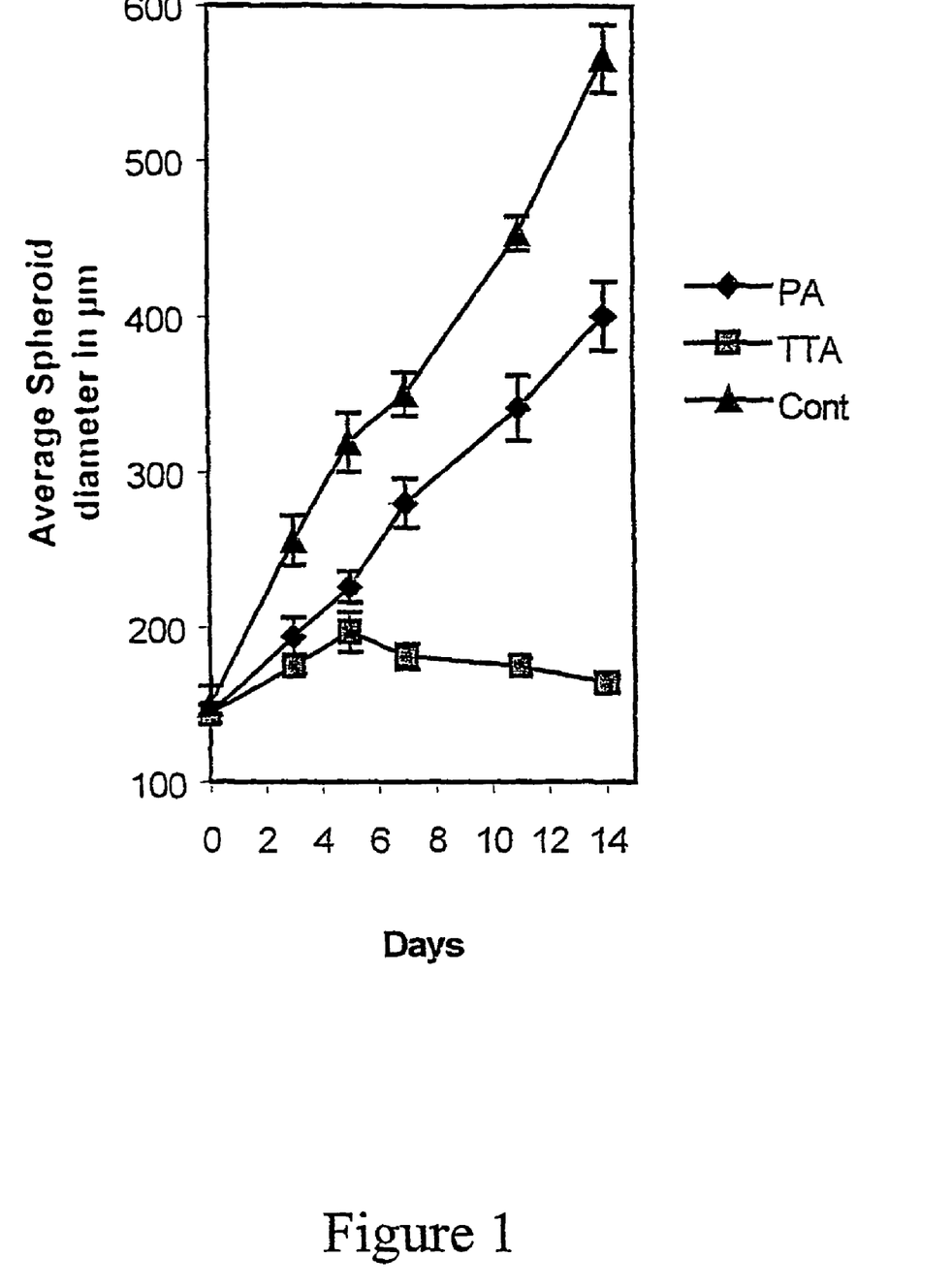
FIG. 1 shows the effect of TTA on the spheroid diameter of D-54Mg spheroids.
Figure 2:
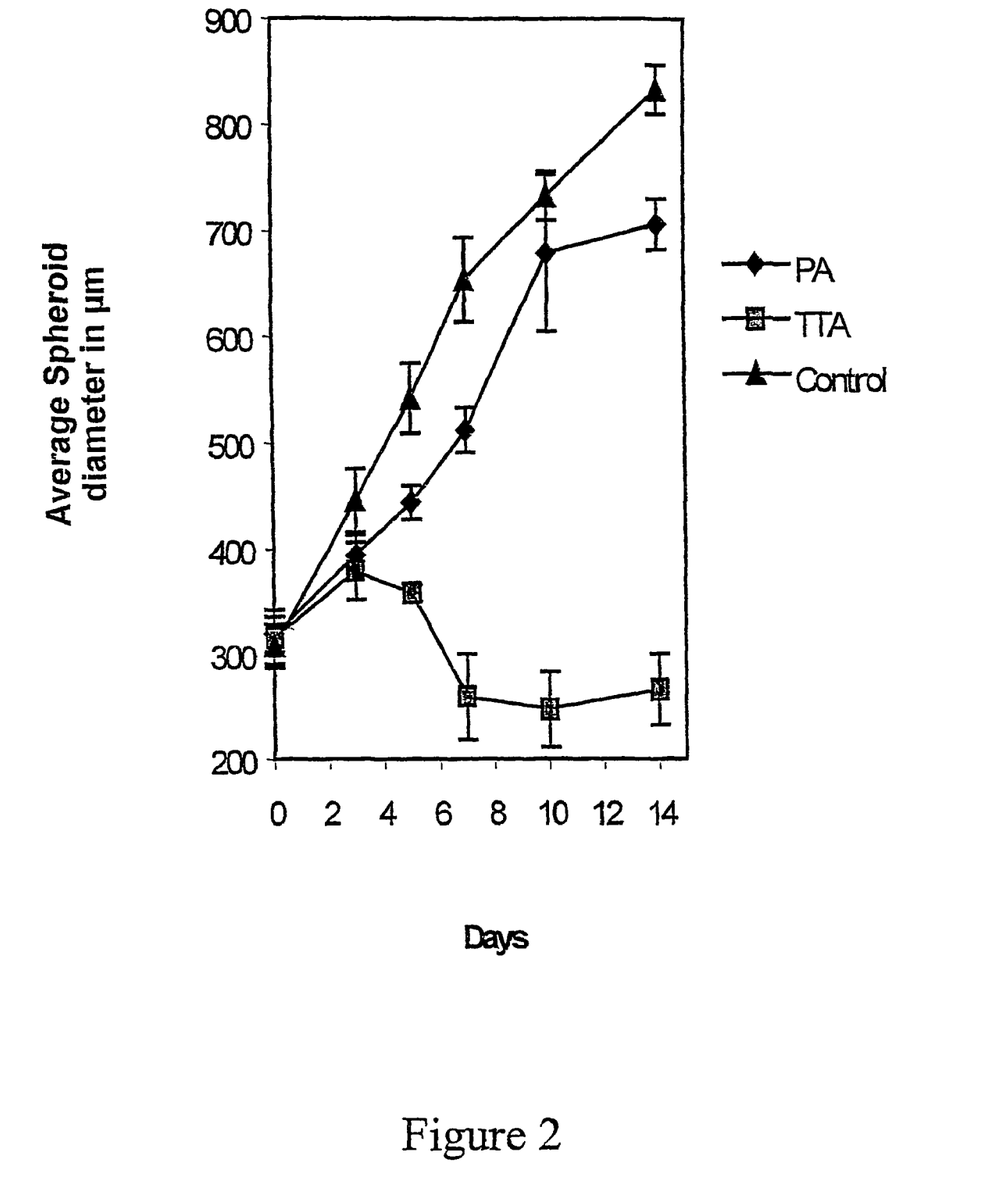
FIG. 2 shows the effect of TTA on the spheroid diameter of GaMg spheroids.
Figure 3:
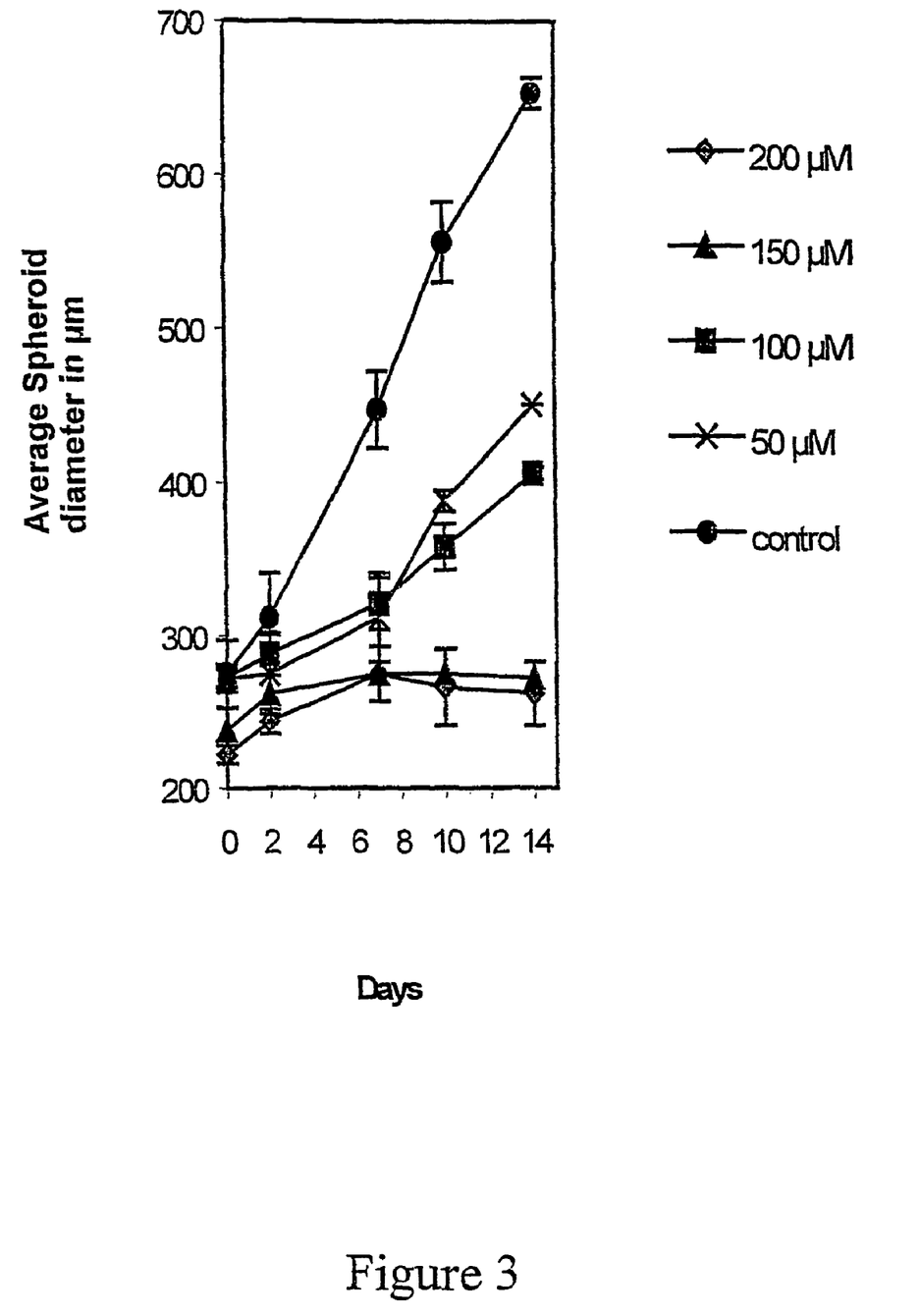
FIG. 3 shows the effect of various concentrations of TTA on the spheroid diameter of D-54Mg spheroids.

The results of these experiments are shown in FIGS. 1-3. As indicated, the fatty acids were exposed to the spheroids during a 14 day long period. No fatty acids were supplemented to the control group (-▲-). The values are presented as mean ± SD.

FIG. 1 shows the effect of 250 µM TTA (-■-) and PA (-♦-) on the average spheroid diameter (µm) of D-54Mg spheroids.

FIG. 2 shows the effect of 250 µM TTA (-■-) and PA (-♦-) on the average spheroid diameter (µm) of GaMg spheroids.

To study the dose dependent effect of TTA on spheroid growth, 24 tumour spheroids from both cell lines were divided into 6 groups which received 0, 50, 100, 150, 200 and 250 µM of TTA. This experiment was performed in SF-X medium (available from Costar, Mass, USA), and the results are given in FIG. 3.

Example 4

Cell Migration

The effect of the fatty acid analogues on cell migration was studied by measuring the ability of cells to migrate out from spheroids that had attached to a plastic surface. GaMg and D-54Mg spheroids with diameters between 200 and 300 µm were transferred individually into 16 mm 24-well dishes. 1.5 ml of DMEM was then added with various concentrations of the different fatty acid analogues. After 3 days of culture the specimens were fixed with 4% formaldehyde on PBS and stained with 2% crystal violet in 96% ethanol. The size of the outgrowth area was then determined by using a Kontron morphometry system (Kontron, Eching, Germany). We used a serum supplemented medium (DMEM) in this assay due to a relative loose attachment of glioma cells to the plastic surface in the SF-X medium. The migratory capacity of the GaMg and D-54MG cells were severely inhibited by TTA at a concentration of 100 µM (data not shown).

Example 5

The Effect of TTA on the Growth of Subcutaneously Implanted BT4Cn Tumours

Mail Norwegian brown rats, BD IX, were obtained from Gades Institute, Haukeland hospital, Bergen, Norway. They were housed in cages, in pairs, and maintained on a 12 h cycle light and dark at a temperature of 20±3° C. During the experiments they weighted 250-400 g. They were fed a commercial standard pelleted food and provided tap water ad libitum. Test groups were treated with TTA, and control groups treated with palmitate and/or carboxymethyl cellulose (CMC).

The TTA was administered by oro-gastric intubation. TTA and PA were suspended in 0.5% (w/v) sodium carboxymethyl cellulose at a final stock solution of 75 mg/ml. The animals were administered once a day at a dose of 300 mg/kg body weight.

The rats were anaesthetised with 0,2 ml Hypnorm-Dormicum/100 g body weight and a tumour was established in vivo, by subcutanously injection of $5*10^6$ tumour cells (in 1 ml NaCl) in the rat's neck. After 3-4 weeks, the tumour was removed and cut into 2*2 mm tissue pieces. The pieces were used for establishment of s.c. tumours in the leg. The rats were anaesthetised with 0.2 ml Hypnorm-Dormicum/100 g body weight, a skin incision was made, and the tissue piece was entered and established approximately 1 cm below the skin incision. The tumours were grown for 2 weeks. The rats were treated either by oro-gastric intubation or by direct injection in tumour.

The volume of the tumours (at leg) were measured.

Figure 4:
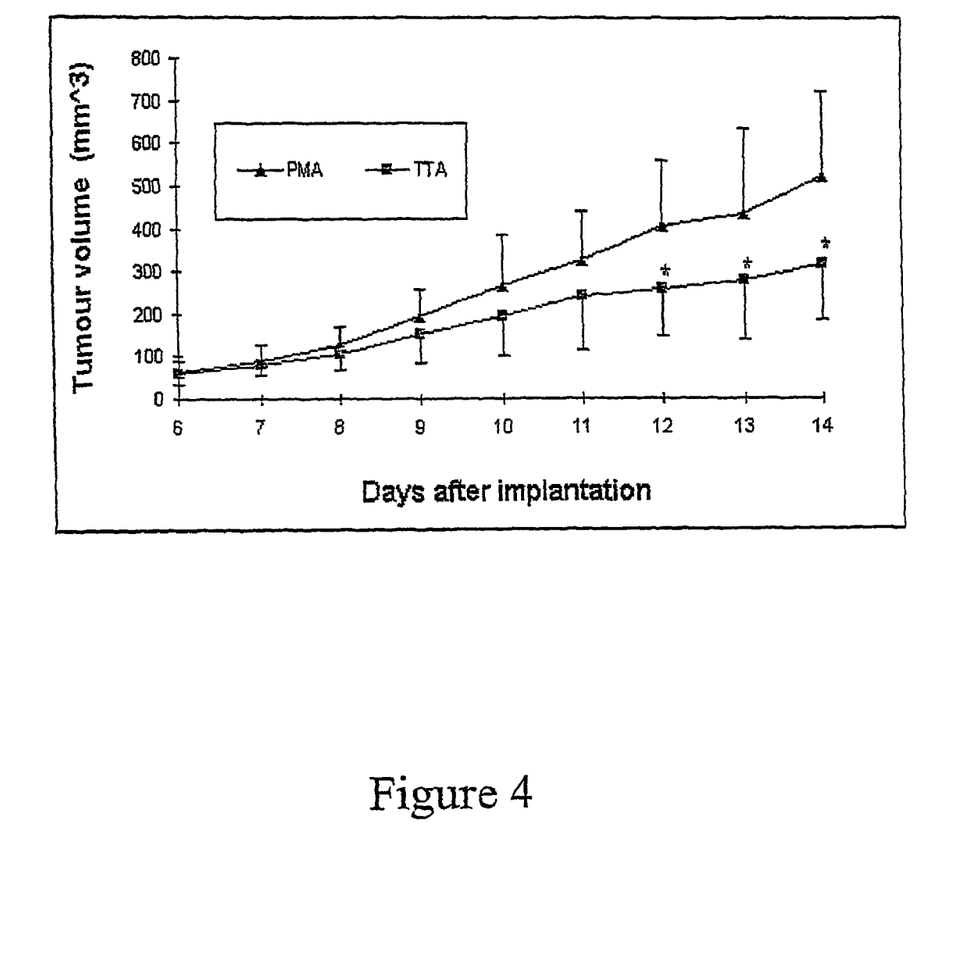
FIG. 4 shows the effect of TTA on the growth of subcutaneously implanted BT4Cn tumours.

FIG. 4 shows the effect of PA () and TTA (—■—) on the growth of subcutaneously implanted BT4Cn tumours.

Example 6

The Effect of TTA on the Survival of Rats With Intracranically Implanted BT4Cn Tumours Mail Norwegian brown rats, BD IX, were used as described in example 5. The TTA was administered by oro-gastric intubation.

The tumour was implanted by stereotactical transplantation. The rats were anaesthetised with 0.4 ml Equithesin/100 g body weight. A skin incision was made, blood was removed by $H_2O_2$ and the scull was trephined using a dental drill.

The burr hole was localized 3.3 mm posterior to the coronal suture and 2.5 mm lateral to the sagittal suture.

Cells were harvested and counted as described above (Section 5.3), and then diluted in DPBS to a final concentration on 20.000 cells/μl. 2 μl cell suspension was injected with a Hamilton syringe with a cone-tipped 0.7 mm needle at a depth of 2.8 mm. The skin was closed with steel staples, and the animals were returned to their cages.

Figure 5:
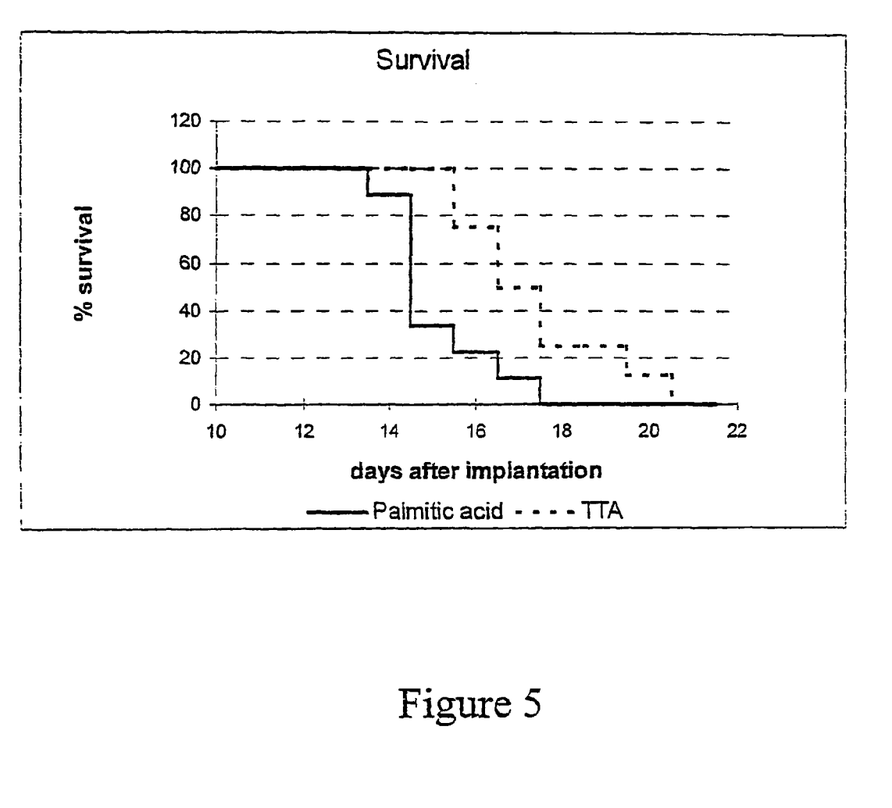
FIG. 5 shows the effect of TTA on the survival of rats with intracranically implanted BT4Cn tumours.

FIG. 5 shows the effect of PA and TTA on the survival of rats with intracranially implanted BT4Cn tumours.

The invention claimed is:

1. A method of inhibiting the metastasis of metastatic neoplasms comprising the administration to a mammal in need thereof an effective amount of a fatty acid analogue having the following formula $$R_1-[x_i-CH_2]_n-COOR_2$$

wherein $R_1$ is;
a $C_2$-$C_{24}$ alkene with one or more double bonds and/or with one or more triple bonds; and/or
a $C_2$-$C_{24}$ alkyne, and/or
a $C_1$-$C_{24}$ alkyl, or a $C_1$-$C_{24}$ alkyl substituted in one or several positions with one a more compounds selected from the group comprising fluoride, chloride, hydroxy, $C_1$-$C_4$ alkoxy, $C_1$-$C_4$ alkylthio, $C_2$-$C_5$ acyloxy or $C_1$-$C_4$ alkyl, and
wherein $R_2$ represents hydrogen or $C_1$-$C_4$ alkyl, and
wherein n is an integer from 2-12, and
wherein i is an odd number and indicates the position relative to $COOR_2$, and
wherein $x_i$ are independently selected from the group consisting of O, S, SO, $SO_2$, Se and $CH_2$, and
with the proviso that at least one of the $x_i$ is not $CH_2$; and
with the proviso that if $R_1$ is an alkyl, then $x_{i=3}$ is not Se or S;
a salt, prodrug or complex thereof, wherein said metastatic neoplasms are sensitive to the effects of said fatty acid analogue.

2. A method as set forth in claim 1, wherein the method is effective to inhibit the invasion of a primary tumor into connective tissue.

3. A method as set forth in claim 1, wherein the method is effective to inhibit the formation of a secondary tumor.

4. A method as set forth in claim 1, wherein the method is effective to increase the survival of a mammal with a tumor due to decrease in the survival-threatening effects of the tumor.

5. A method as set forth in claim 1, wherein the method is effective to maintain a therapeutically effective concentration substantially continuously in the blood of the mammal during the period of administration.

6. A method as set forth in claim 1, wherein the fatty acid analogue is administered in unit dosage forms.

7. A method of treating the metastasis of metastatic neoplasms comprising the administration to a mammal in need thereof an effective amount of a fatty acid analogue having the following formula $$R_1-[x_i-CH_2]_n-COOR_2$$

wherein $R_1$ is;
a $C_2$-$C_{24}$ alkene with one or more double bonds and/or with one a more triple bonds, end/or
$C_2$-$C_{24}$ alkyne, and/or
$C_1$-$C_{24}$ alkyl, or a $C_1$-$C_{24}$ alkyl substituted in one or several positions with one or more compounds selected from the group comprising fluoride, chloride, hydroxy, $C_1$-$C_4$ alkoxy, $C_2$-$C_4$ alkyltliio, $C_2$-$C_5$ acyloxy or $C_1$-$C_4$ alkyl, and
wherein $R_2$ represents hydrogen or $C_1$-$C_4$ alkyl, and
wherein n is an integer from 1-12, and
wherein i is an odd number and indicates the position relative to $COOR_2$, and
wherein $x_i$ are independently selected from the group consisting of O, S, SO, $SO_2$, Se and $CH_2$, and
with the proviso that at least one of the $x_1$ is not $CR_2$;
a salt, prodrug or complex thereof, wherein said metastatic neoplasms are sensitive to the effects of said fatty acid analogue.

8. A method as set forth in claim 7, wherein the fatty acid analogue is tetradecylthioacetic acid.

9. A method as set forth in claim 7, wherein the fatty acid analogue is tetradecylselenoacetic acid.

10. A method as set forth in claim 7, wherein the treatment is effective to inhibit the invasion of a primary tumor into connective tissue.

11. A method as set forth in claim 7, herein the treatment is effective to inhibit the formation of a secondary tumor.

12. A method as set forth in claim 7, wherein the treatment is effective to increase the survival of a mammal with a tumor due to decrease in the survival-threatening effects of the tumor.

13. A method as set forth in claim 7, wherein the treatment is effective to maintain a therapeutically effective concentration substantially continuously in the blood of the mammal during the period of administration.

14. A method as set forth in claim 7, wherein the fatty acid analogue is administered in unit dosage forms.

15. A method of inhibiting the metastasis of metastatic neoplasms comprising the administration to a mammal in need thereof an effective amount of a fatty acid analogue having the following formula wherein $R_1$ is;
a $C_1$-$C_{24}$ alkyl, and
wherein $R_2$ represents hydrogen or $C_1$-$C_4$ alkyl, and
wherein x is independently selected from the group consisting of S and Se;
a salt, prodrug or complex thereof, wherein said metastatic neoplasms are sensitive to the effects of said fatty acid analogue.

16. The method as set forth in claim 15, wherein the fatty acid analogue is tetradecylthioacetic acid.

17. The method as set forth in claim 15, wherein the fatty acid analogue is tetradecylselenoacetic acid.

18. The method as set forth in claim 15, wherein the method is effective to inhibit the invasion of a primary tumor into connective tissue.

19. The method as set forth in claim 15, wherein the method is effective to inhibit the formation of a secondary tumor.

20. The method as set forth in claim 15, wherein the method is effective to increase the survival of a mammal with a tumor due to decrease in the survival-threatening effects of the tumor.

21. The method as set forth in claim 15, wherein the method is effective to maintain a therapeutically effective concentration substantially continuously in the blood of the mammal during the period of administration.

22. The method as set forth in claim 15, wherein the fatty acid analogue is administered in unit dosage forms.

* * * * *